United States Patent
Tanaka et al.

(10) Patent No.: US 10,203,291 B2
(45) Date of Patent: Feb. 12, 2019

(54) METHOD FOR EVALUATING ARC-RESISTANCE PERFORMANCE AND ARC-RESISTANCE PERFORMANCE EVALUATION DEVICE

(71) Applicant: Kaneka Corporation, Osaka (JP)

(72) Inventors: Yasunori Tanaka, Ishikawa (JP); Masahiro Ishida, Ishikawa (JP); Hiroyasu Hagi, Hyogo (JP); Atsushi Mizobuchi, Osaka (JP)

(73) Assignee: Kaneka Corporation (JP)

( * ) Notice: Subject to any disclaimer, the term of this patent is extended or adjusted under 35 U.S.C. 154(b) by 307 days.

(21) Appl. No.: 14/895,743

(22) PCT Filed: May 27, 2014

(86) PCT No.: PCT/JP2014/063999
§ 371 (c)(1),
(2) Date: Dec. 3, 2015

(87) PCT Pub. No.: WO2014/203692
PCT Pub. Date: Dec. 24, 2014

(65) Prior Publication Data
US 2016/0123912 A1 May 5, 2016

(30) Foreign Application Priority Data

Jun. 21, 2013 (JP) ................................. 2013-130527

(51) Int. Cl.
*G01N 17/00* (2006.01)
*G01N 3/60* (2006.01)
(Continued)

(52) U.S. Cl.
CPC ........... *G01N 25/18* (2013.01); *G01N 33/367* (2013.01); *H05H 1/30* (2013.01)

(58) Field of Classification Search
USPC .............................. 374/141, 208, 179, 44, 57
See application file for complete search history.

(56) References Cited

U.S. PATENT DOCUMENTS 5,254,829 A * 10/1993 Drouet ................... B23K 10/00
219/121.39
2006/0283549 A1* 12/2006 Aramaki ........... H01J 37/32091
156/345.28
(Continued)

FOREIGN PATENT DOCUMENTS

| JP | 2003244811 A | 8/2003 |
| JP | 2004077205 A | 3/2004 |
| JP | 2010225308 A | 10/2010 |

OTHER PUBLICATIONS

Translation of JP 2010-225308 (Oct. 7, 2010).*
(Continued)

*Primary Examiner* — Mirellys Jagan
(74) *Attorney, Agent, or Firm* — Lerner, David, Littenberg, Krumholz & Mentlik, LLP

(57) ABSTRACT

An arc-resistance performance evaluation device includes a plasma generator that generates plasma; and a stand on which a sheet-like test piece is placed so that the plasma generated in the plasma generator is irradiated on a front surface of said test piece, the stand includes a temperature measurement device that measures a temperature on a back surface of said test piece.

8 Claims, 8 Drawing Sheets

(51) Int. Cl.
  *G01K 7/00*   (2006.01)
  *G01N 25/18*  (2006.01)
  *G01N 33/36*  (2006.01)
  *H05H 1/30*   (2006.01)

(56) References Cited

U.S. PATENT DOCUMENTS

2008/0280451 A1* 11/2008 Ohmoto ............ H01L 21/67109
                                                    438/710
2013/0241582 A1*  9/2013 Tanaka ................... G01R 27/02
                                                    324/703
2016/0326692 A1* 11/2016 Gladish ................ D06P 5/2011

OTHER PUBLICATIONS

Translation of JP 2003-244811 (Aug. 29, 2003).*
International Search Report for Application No. PCT/JP2014/063999 dated Sep. 2, 2014.
International Preliminary Report on Patentability, Chapter I, for Application No. PCT/JP2014/063999 dated Dec. 22, 2015.

* cited by examiner

METHOD FOR EVALUATING ARC-RESISTANCE PERFORMANCE AND ARC-RESISTANCE PERFORMANCE EVALUATION DEVICE

CROSS-REFERENCE TO RELATED APPLICATIONS

The present application is a national phase entry under 35 U.S.C. § 371 of International Application No. PCT/JP2014/063999, filed May 27, 2014, which claims priority from Japanese Patent Application No. 2013-130527, filed Jun. 21, 2013, all of which are hereby incorporated herein by reference.

TECHNICAL FIELD

The present invention relates to a method for evaluating arc-resistance performance wherein temperature of test pieces irradiated with plasma is measured, and to an arc-resistance performance evaluation device that measures temperature of test pieces irradiated with plasma.

BACKGROUND ART

In the U.S., five to ten arc flash incidents happen per day. Such incidents can cause severe burn injuries or fatalities of workers due to very high arc temperatures of no less than about 5000 K. Therefore, protective clothing with high arc-resistance performance is desired for body protection from such incidents. For the development of such protective clothing, it is necessary to investigate what material should be used for the clothing fabric.

Conventionally, an arc-resistance performance evaluation device that measures the temperatures on the surface and inside of a test piece irradiated with plasma is known (such as Patent Document 1), as one of arc-resistance performance evaluation devices for evaluating arc-resistance performance of clothing fabrics. Such an arc-resistance performance evaluation device measures the temperature inside the test piece (or estimates the inside temperature of the test piece by measuring the surface temperature of the test piece), whereby the heat energy input to the test piece can be determined.

In order to prevent workers' severe burn injuries or the like, it is important to know the temperature on the inner surface of the protective clothing that comes into contact with the worker's skin. However, the arc-resistance performance evaluation device according to Patent Document 1 determines (or estimates) the inside temperature of the test piece, i.e., the inside temperature of the protective clothing. Therefore, the arc-resistance performance of protective clothing cannot be evaluated appropriately based on the heat energy that will be input to the worker wearing the clothing with such an arc-resistance performance evaluation device.

PRIOR ART DOCUMENTS

Patent Documents

Patent Document 1: JP-A-2004-77205

SUMMARY OF THE INVENTION

Problems to be Solved by the Invention

In view of such circumstances, an object of the present invention is to provide a method for evaluating arc-resistance performance and an arc-resistance performance evaluation device, with which the arc-resistance performance of protective clothing can be evaluated appropriately based on the heat energy that will be input to the worker wearing the clothing.

Means for Solving the Problems

According to the present invention, there is provided a method for evaluating arc-resistance performance, which includes:
  irradiating a front surface of a sheet-like test piece with plasma;
  measuring a temperature on a back surface of said test piece irradiated with the plasma;
  calculating a temperature rise rate based on the measured temperature; and
  evaluating arc-resistance performance based on the calculated temperature rise rate.

According to the method for evaluating arc-resistance performance of the present invention, the front surface of a sheet-like test piece is irradiated with plasma, and the temperature on the back surface of this test piece is measured. A temperature rise rate is calculated based on the measured temperature, and the arc-resistance performance is evaluated based on the calculated temperature rise rate. Since the arc-resistance performance is evaluated based on the temperature on the back surface of the test piece, the arc-resistance performance of protective clothing can be evaluated appropriately based on the heat energy that will be input to the worker wearing the clothing.

Also, the method for evaluating arc-resistance performance of the present invention may have a configuration in which:
  said plasma is inductively coupled thermal plasma.

According to the present invention, there is provided an arc-resistance performance evaluation device, which includes:
  a plasma generator that generates plasma; and
  a stand on which a sheet-like test piece is placed so that the plasma generated in the plasma generator is irradiated on a front surface of said test piece,
  wherein said stand includes a temperature measurement device that measures a temperature on a back surface of said test piece.

According to the arc-resistance performance evaluation device of the present invention, the plasma generator generates plasma, and the stand sets the sheet-like test piece in position, so that the plasma generated by the plasma generator is irradiated on the front surface of the test piece. The temperature measurement device then measures the temperature on the back surface of the test piece. Arc-resistance performance evaluation based on the back surface temperature of the test piece is thus made possible, so that the arc-resistance performance of protective clothing can be evaluated appropriately based on the heat energy that will be input to the worker wearing the clothing.

Also, the arc-resistance performance evaluation device of the present invention may have a configuration in which:
  said temperature measurement device includes a thermocouple that detects temperature, and a flat plate-like heat conducting part that supports the back surface of said test piece and conducts heat from the back surface of said test piece to said thermocouple.

With this configuration, the plate-like heat conducting part supports the back surface of the test piece. The heat conducting part conducts the heat of the back surface of the test piece to the thermocouple, which detects the temperature. This way, the temperature on the back surface of the test piece can be measured accurately.

Also, the arc-resistance performance evaluation device of the present invention may have a configuration in which:
said stand includes a base body for fixing said heat conducting part, and a heat insulating part having lower heat conductivity than that of said base body and disposed between said base body and said heat conducting part.

With this configuration, the base body fixes the heat conducting part. The heat insulating part having lower heat conductivity than that of the base body is disposed between the base body and the heat conducting part. The heat conduction from the base body to the heat conducting part is thus reduced, so that the temperature on the back surface of the test piece can be measured accurately via the heat conducting part with the thermocouple.

Also, the arc-resistance performance evaluation device of the present invention may include:
a calculation unit that calculates a temperature rise rate based on the temperature measured by said temperature measurement device; and
an evaluation unit that evaluates arc-resistance performance based on the temperature rise rate calculated by said calculation unit.

With this configuration, the calculation unit calculates a temperature rise rate based on the temperature measured by the temperature measurement device. The evaluation unit evaluates the arc-resistance performance based on the temperature rise rate calculated by the calculation unit. Since the arc-resistance performance is evaluated based on the temperature on the back surface of the test piece, the arc-resistance performance of protective clothing can be evaluated appropriately based on the heat energy that will be input to the worker wearing the clothing.

Also, the arc-resistance performance evaluation device of the present invention may have a configuration in which:
said plasma is inductively coupled thermal plasma.

Effect of the Invention

As described above, the present invention provides the excellent effect of enabling appropriate evaluation of the arc-resistance performance of protective clothing based on the heat energy that will be input to the worker wearing the clothing.

MODE FOR CARRYING OUT THE INVENTION

Hereinafter, one embodiment of the arc-resistance performance evaluation device according to the present invention will be described with reference to FIG. 1 to FIG. 10.

Figure 1:
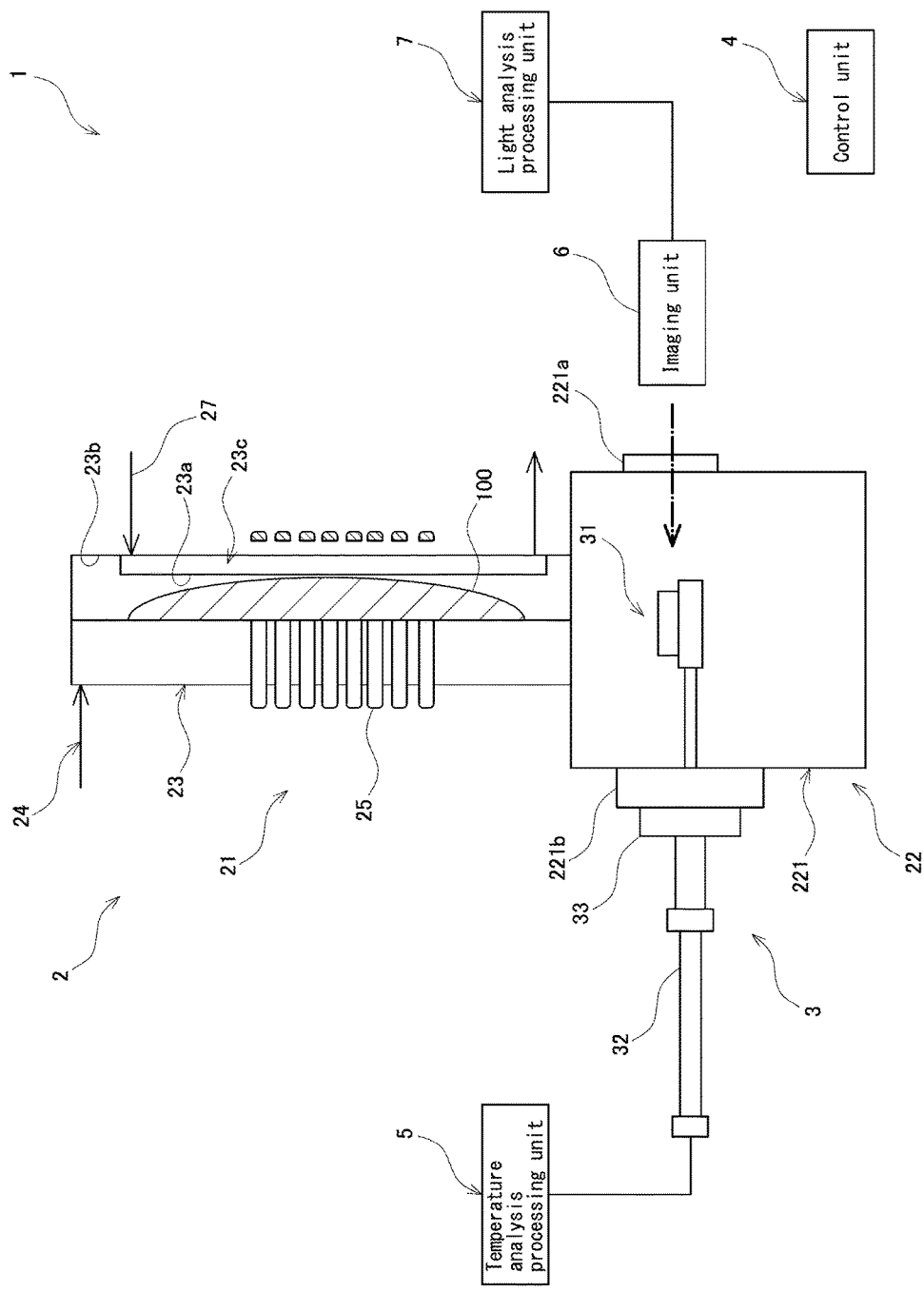
FIG. 1 is a schematic overall diagram with a partial internal view of an arc-resistance performance evaluation device according to one embodiment of the present invention.

As shown in FIG. 1, the arc-resistance performance evaluation device 1 according to this embodiment includes a device main body 2 that generates plasma 100, a stand unit 3 for setting a sheet-like test piece 10 in position, and a control unit 4 that controls the device main body 2. The arc-resistance performance evaluation device 1 includes a temperature analysis processing unit 5 that analyzes and processes the temperature of a test piece 10, an imaging unit 6 that takes pictures of the test piece 10, and a light analysis processing unit 7 that analyzes the state of the test piece 10. The arc-resistance performance evaluation device 1 includes a setting value input unit 8 for inputting various setting values.

The device main body 2 includes a plasma generator 21 that generates plasma 100, and a chamber unit 22 that is disposed below the plasma generator 21 and accommodates the test piece 10 irradiated with the plasma 100. The arc-resistance performance evaluation device 1 according to this embodiment is configured to irradiate the test piece 10 with inductively coupled thermal plasma (ICTP) instead of arc plasma.

Figure 2:
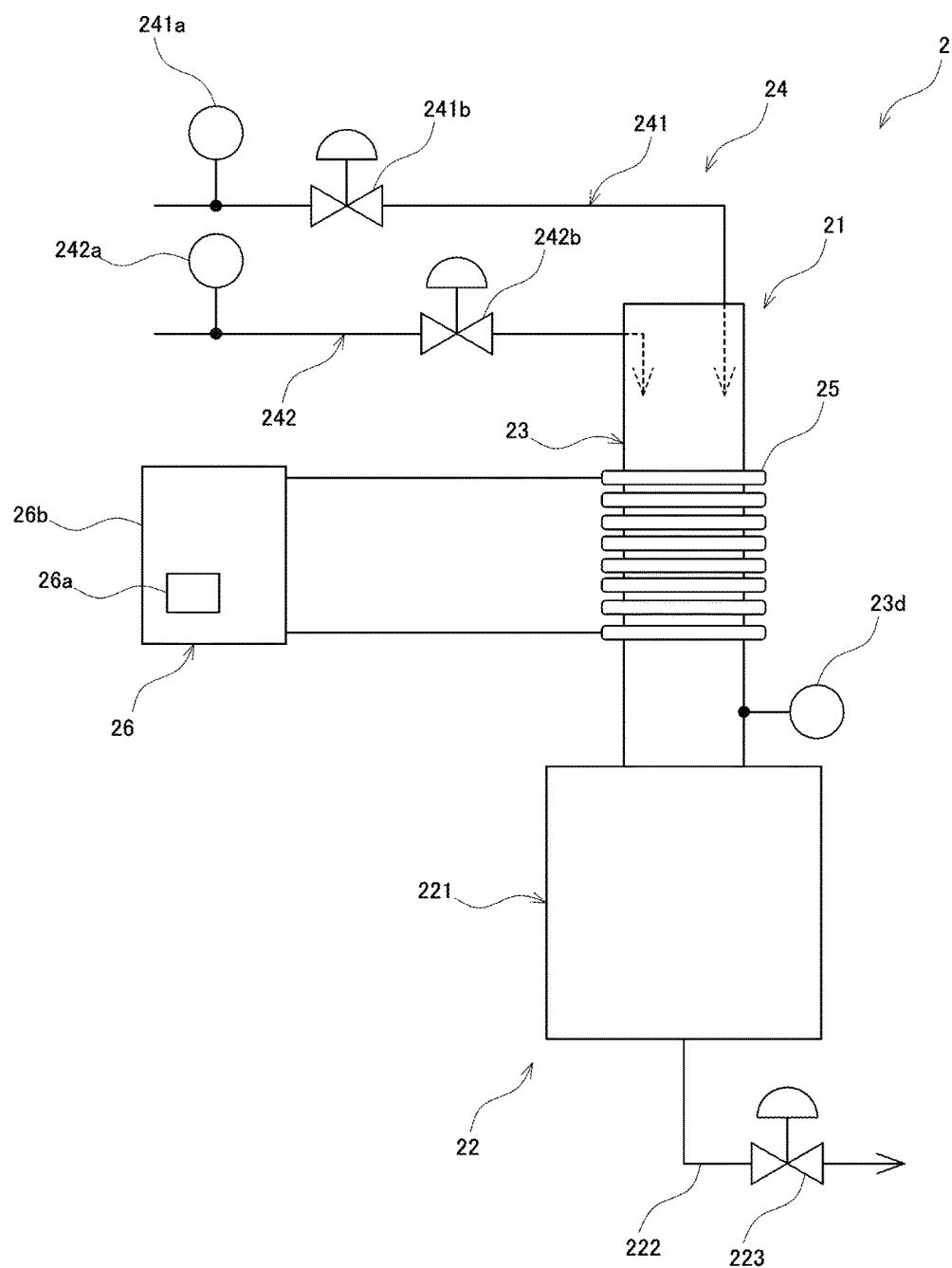
FIG. 2 is a schematic diagram of essential parts of the arc-resistance performance evaluation device according to the same embodiment.

The plasma generator 21 includes, as shown in FIG. 1 and FIG. 2, a tubular part 23 for generating plasma 100, a gas inlet 24 for introducing a gas into the tubular part 23, and an induction coil 25 wound on the outer circumference of the tubular part 23. The plasma generator 21 includes a power source 26 for supplying power to the induction coil 25, and a cold water supply unit 27 for cooling the tubular part 23.

The tubular part 23 is formed to have a double tube structure, with an inner tube 23a and an outer tube 23b. The tubular part 23 includes a flow passage 23c for the cold water supplied from the cold water supply unit 27 to pass through between the inner tube 23a and the outer tube 23b so as to cool the tubular part 23 heated with the plasma 100. The tubular part 23 includes a pressure detector 23d that detects pressure inside the tubular part. The pressure detector 23d outputs detected pressure to the control unit 4 and displays the detected pressure value.

The gas inlet 24 includes a first gas inlet part 241 that introduces an outer radial gas, and a second gas inlet part 242 that introduces an outer swirling gas. The outer radial gas is a stream of gas that flows axially along the inner wall of the tubular part 23, while the outer swirling gas is a stream of gas that flows spirally in the axial direction along the inner wall of the tubular part 23.

The gas inlet 24 includes incoming flow rate detectors 241a and 242a that detect the flow rate of gas flowing into the tubular part 23, and incoming flow rate changers 241b and 242b that change the flow rate of gas flowing into the tubular part 23. In this embodiment, the incoming flow rate changers 241b and 242b are flow control valves that change the flow rate of gas by the degree of opening.

The incoming flow rate detectors 241a and 242a are respectively provided to the gas inlet parts 241 and 242. The incoming flow rate detectors 241a and 242a each detect the flow rate in the gas inlet parts 241 and 242, respectively. The incoming flow rate detectors 241a and 242a each output detected flow rate to the control unit 4 and display the detected flow rate values.

The induction coil 25 consists of several turns (eight turns in this embodiment) around the outer circumference of the tubular part 23. With the gas introduced from the gas inlet 24 contained inside the tubular part 23, a high frequency current is applied to the induction coil 25, whereby plasma 100 is generated inside the tubular part 23. More specifically, what happens is as follows:

A high frequency current applied to the induction coil 25 creates an alternating magnetic field along an axial direction inside the tubular part 23. This magnetic field induces an alternating electric field in a radial direction inside the tubular part 23. In this state, when a predetermined sheath gas stream is introduced from the gas inlet 24, plasma 100 is generated along the axial direction of the tubular part 23 by excitation and electrolytic dissociation of the sheath gas inside the tubular part 23. The plasma 100 is stably maintained inside the tubular part 23 due to the high frequency current produced as a result of the alternating electric fields inside the generated plasma 100.

The power source 26 includes a power detector 26a that detects the electrical power supplied to the induction coil 25, and a power changer 26b that changes the level of power supplied to the induction coil 25. The power detector 26a outputs detected electrical power to the control unit 4 and displays the detected electrical power value.

The chamber unit 22 includes a chamber 221 having a space for accommodating the test piece 10 inside. The chamber unit 22 includes a gas outlet 222 for discharging the gas inside the chamber 221 to the outside, and an outgoing flow rate changer 223 that changes the flow rate of gas discharged from the gas outlet 222. In this embodiment, the outgoing flow rate changer 223 is a flow control valve that changes the flow rate of gas by the degree of opening.

The chamber 221 includes a window 221a for allowing observation of the inside, so that the imaging unit 6 disposed outside can take pictures of the test piece 10 disposed inside. The chamber 221 includes an insertion part 221b for allowing insertion of the test piece 10 placed on the stand unit 3 from the outside to the inside.

The stand unit 3 includes a stand 31 on which the test piece 10 is placed, so that the plasma 100 generated in the plasma generator 21 is irradiated on the front surface of the sheet-like test piece 10. The stand unit 3 includes a movable part 32 movable between a reference position where the test piece 10 is irradiated with the plasma 100 and a retracted position where the test piece 10 is prevented from being irradiated with the plasma 100, and a fixed part 33 fixed to the insertion part 221b of the chamber 221.

Figure 3:
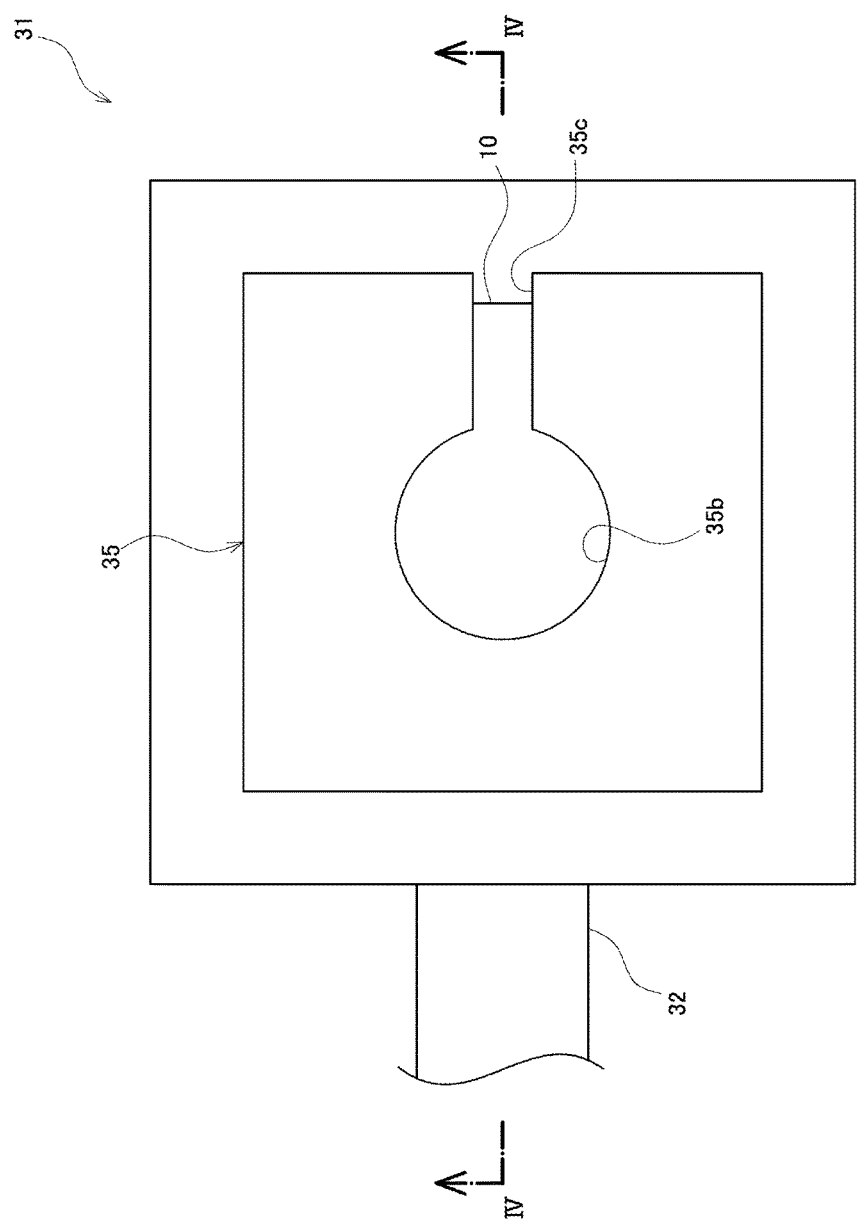
FIG. 3 is an overall plan view of a stand according to the same embodiment.
Figure 4:
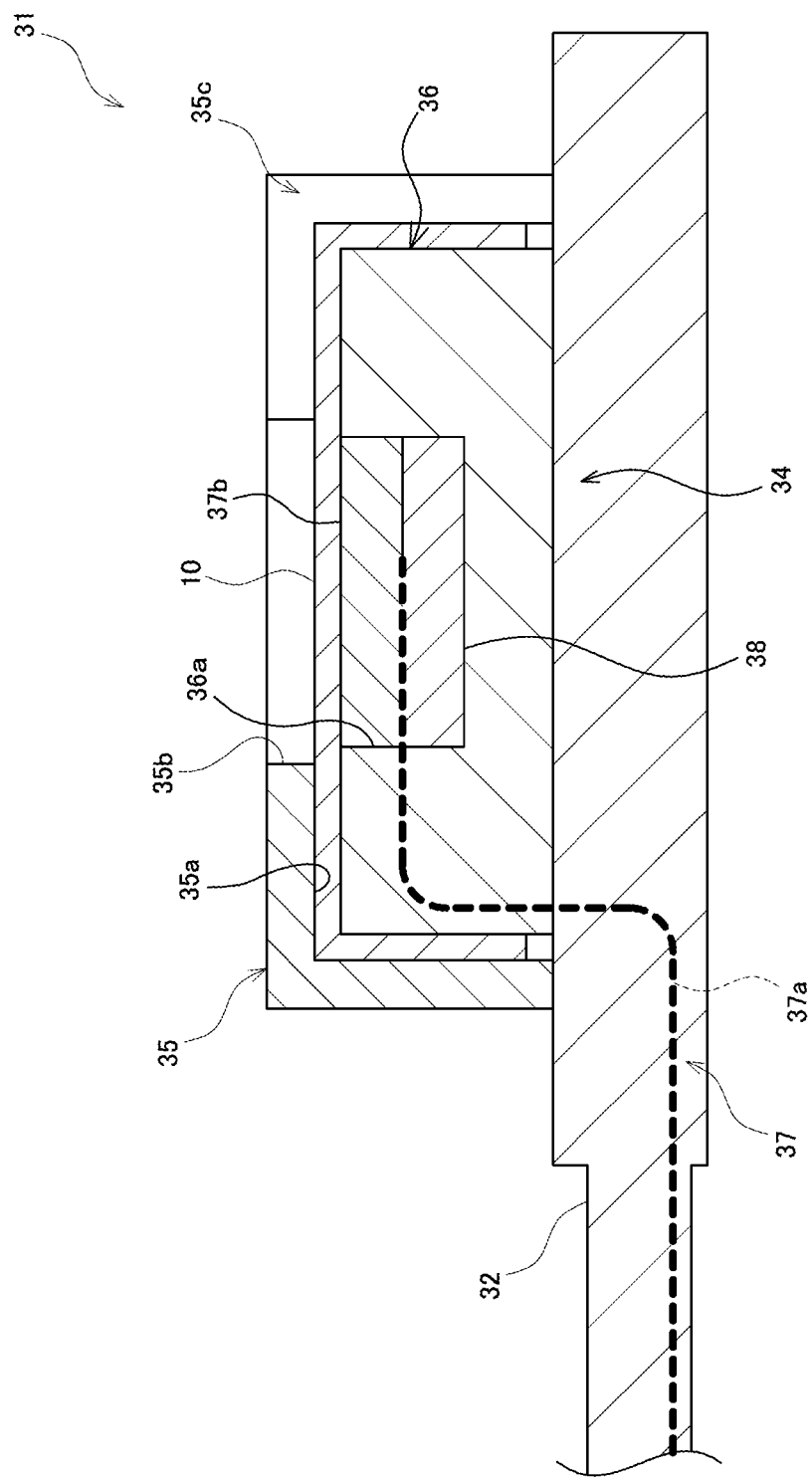
FIG. 4 is a cross-sectional view along line IV-IV in FIG. 3 of the stand according to the same embodiment.

The stand 31 includes a base 34 on which the test piece 10 sits, and a cover 35 that holds the test piece 10 set on the base 34 such as to cover the test piece 10, as shown in FIG. 3 and FIG. 4. The stand 31 includes a fixing mechanism (not shown) such as screws and the like for fixing the cover 35 to the base 34.

The base 34 includes a base body 36 connected to the distal end of the movable part 32, and a temperature measurement device 37 that is fixed to the base body 36 and measures the temperature on the back surface of the test piece 10. The base 34 includes a heat insulating part 38 having lower heat conductivity than that of the base body 36 so that less heat is conducted from the base body 36 to the temperature measurement device 37.

The base body 36 includes a cavity 36a for housing the temperature measurement device 37 and the heat insulating part 38 in an upper central portion. The base body 36 is formed rectangular and fitted with the cover 35 from above, with the test piece 10 therebetween. The base body 36 thus stops the cover 35 from rotating in the up and down direction. In this embodiment, the base body 36 is made of stainless steel.

The temperature measurement device 37 includes a thermocouple 37a that detects temperature, and a flat plate-like heat conducting part 37b that supports the back surface of the test piece 10 and conducts the heat from the back surface of the test piece 10 to the thermocouple 37a. One end of the thermocouple 37a is connected to a lower face of the heat conducting part 37b. The other end of the thermocouple 37a is connected to the temperature analysis processing unit 5. In this embodiment, the thermocouple 37a is of a K type.

The heat conducting part 37b is disposed in an upper part of the base 34 such that upper face of the heat conducting part 37b forms the upper face of the base 34. This way, the heat conducting part 37b is in contact with the back surface of the test piece 10 set on the base 34. More specifically, the entire upper face of the heat conducting part 37b is in contact with the back surface of the test piece 10. In this embodiment, the heat conducting part 37b is made of copper.

The heat insulating part 38 is disposed between the base body 36 and the heat conducting part 37b. The heat insulating part 38 is disposed such as to cover the entire lower face of the heat conducting part 37b and sandwiches the thermocouple 37a with the heat conducting part 37b. In this embodiment, the heat insulating part 38 is made of polytetrafluoroethylene (PTFE).

The cover 35 includes a holder 35a that holds the front surface of the test piece 10 set on the base 34. The cover 35 includes a circular opening 35b in an upper part for exposing part of the front surface of the test piece 10 so that the plasma 100 generated in the plasma generator 21 can irradiate the front surface of the test piece 10. The cover 35 includes a groove 35c in a side part for exposing part of the front surface of the test piece 10 along the up and down direction so that the imaging unit 6 can take pictures of the front surface of the test piece 10 from a lateral direction. In this embodiment, the cover 35 is made of stainless steel.

Figure 5:
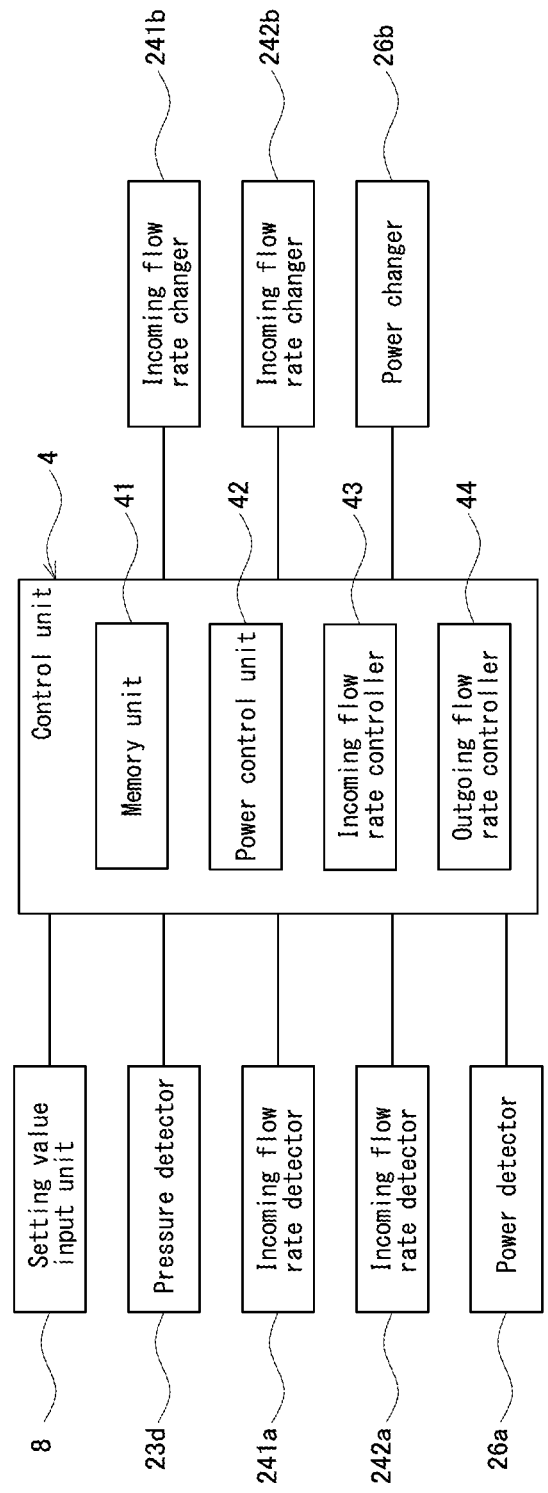
FIG. 5 is a block diagram of the arc-resistance performance evaluation device according to the same embodiment.

The control unit 4 includes, as shown in FIG. 5, a memory unit 41 that stores setting values input from the setting value input unit 8 (values of electrical power supplied to the induction coil 25, flow rate of gas introduced into the tubular part 23, and pressure values inside the tubular part 23). The control unit 4 includes a power control unit 42 that controls the power changer 26b based on the power detected by the power detector 26a so that the power supplied to the induction coil 25 stays constant at a preset level.

The control unit 4 includes an incoming flow rate controller 43 that controls the incoming flow rate changers 241b and 242b based on the flow rate detected by the incoming flow rate detectors 241a and 242a so that the flow rate in each of the gas inlet parts 241 and 242 stays constant at a preset level. The control unit 4 includes an outgoing flow rate controller 44 that controls the outgoing flow rate changer 223 so that the pressure inside the tubular part 23 stays constant at a preset level.

Figure 6:
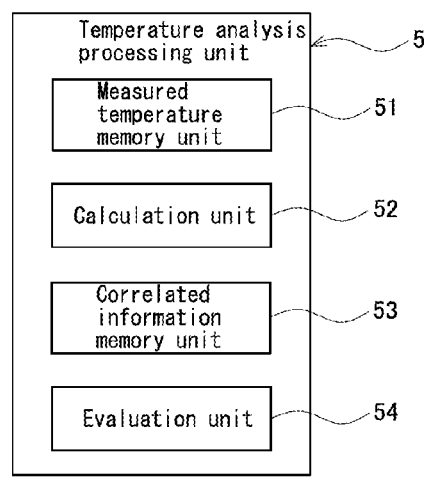
FIG. 6 is a block diagram of a temperature analysis processing unit according to the same embodiment.

The temperature analysis processing unit 5 includes a measured temperature memory unit 51 that stores temperatures measured by the temperature measurement device 37, as shown in FIG. 6. The temperature analysis processing unit 5 includes a calculation unit 52 that calculates temperature rise rates based on the temperatures measured by the temperature measurement device 37. The temperature analysis processing unit 5 includes a correlated information memory unit 53 that stores information on correlation between the temperature rise rate and the arc-resistance performance, and an evaluation unit 54 that evaluates arc-resistance performance based on the temperature rise rate calculated by the calculation unit 52 and the information stored in the correlated information memory unit 53.

Referring back to FIG. 1, the imaging unit 6 is disposed outside and on one side of the chamber 221. The imaging unit 6 takes pictures of the statuses of the test piece 10 through the window 221a of the chamber 221 and the groove 35c of the cover 35. More specifically, the imaging unit 6 takes pictures of how ablated vapor is generated from the test piece 10. In this embodiment, the imaging unit 6 is a high-speed color video camera.

Figure 7:
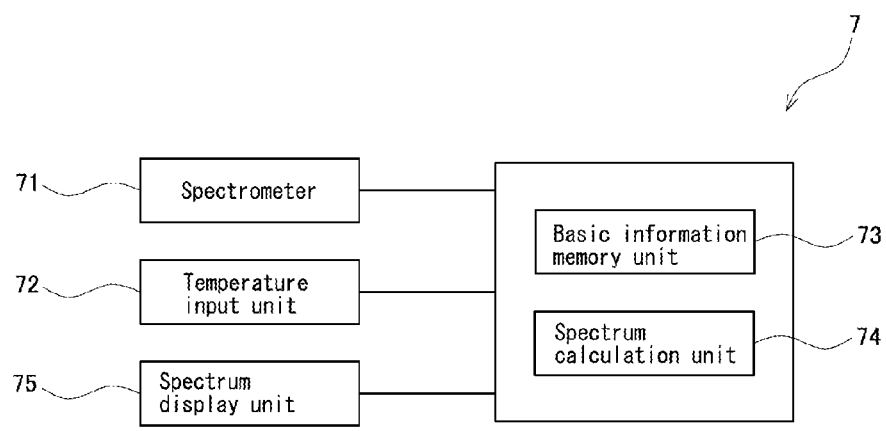
FIG. 7 is a block diagram of a light analysis processing unit according to the same embodiment.

The light analysis processing unit 7 includes a spectrometer 71 that calculates analytical spectral shapes from images of ablated vapor as shown in FIG. 7. The light analysis processing unit 7 includes a temperature input unit 72 for inputting oscillating temperatures or rotational temperatures, and a basic information memory unit 73 that stores basic information (such as formulas) for calculating spectral shapes. The light analysis processing unit 7 includes a spectrum calculation unit 74 for calculating theoretical spectral shapes based on the oscillating temperatures or rotational temperatures input at the temperature input unit 72 and the basic information stored in the basic information memory unit 73.

The light analysis processing unit 7 includes a spectrum display unit 75 for displaying analytical spectral shapes calculated by the spectrometer 71 and theoretical spectral shapes calculated by the spectrum calculation unit 74. The spectrum display unit 75 displays analytical spectral shapes and theoretical spectral shapes superposed upon one another. An analyst determines a theoretical spectral shape that best matches or is closest to the analytical spectral shape (performs a fitting process), whereby oscillating temperatures or rotational temperatures of constituent elements can be calculated.

Instead of the above-described configuration wherein an analyst makes determination, the spectrum calculation unit 74 may be configured such that the spectrum calculation unit 74 determines a theoretical spectral shape that satisfies preset conditions and causes the spectrum display unit 75 to display the specified theoretical spectral shape superposed upon the analytical spectral shape. An example of preset conditions is, for example, having a largest area overlapping the analytical spectral shape within a predetermined frequency range.

The arc-resistance performance evaluation device 1 according to this embodiment is configured as described above. Next, the method for evaluating arc-resistance performance according to this embodiment will be described with reference to FIG. 8.

Figure 8:
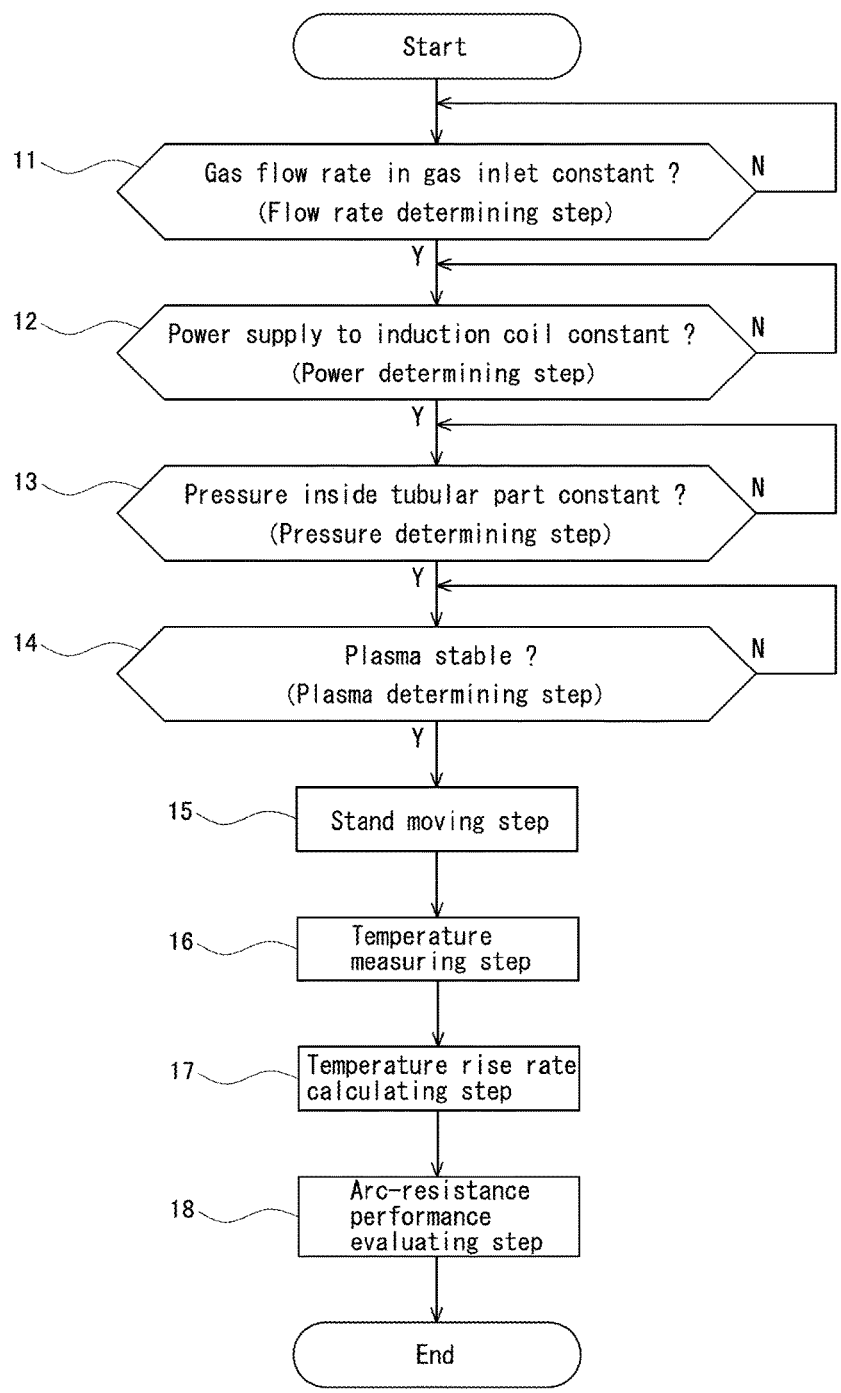
FIG. 8 is a flowchart of a method for evaluating arc-resistance performance according to the same embodiment.

As shown in FIG. 8, the flow rates of gases flowing through the gas inlet parts 241 and 242 are checked with the incoming flow rate detectors 241a and 242a, to determine whether or not a first requirement that the flow rates in the gas inlet parts 241 and 242 are in a constant state is met (flow rate determining step 11). Next, the power supplied to the induction coil 25 is checked with the power detector 26a, to determine whether or not a second requirement that the power supplied to the induction coil 25 is in a constant state is met (power determining step 12).

Then, the pressure inside the tubular part 23 is checked with the pressure detector 23d, to determine whether or not a third requirement that the pressure inside the tubular part 23 is in a constant state is met (pressure determining step 13). Furthermore, the state of plasma 100 in the tubular part 23, inside of which can be observed, is checked from the outside, to determine whether or not a fourth requirement that the plasma 100 is in a stable state is met (plasma determining step 14). If the plasma 100 is emitting light with little flickering and not contacting the inner wall of the tubular part 23, it is determined that the plasma 100 is in a stable state.

If all of the four requirements described above are met, the stand 31 is moved from the retracted position to the reference position by operating the movable part 32 (stand moving step 15). The temperature measurement device 37 measures the temperature on the back surface of the test piece 10 during a preset period of time (for example, 5 seconds) when the front surface of the test piece 10 located at the reference position is irradiated with the plasma 100 (temperature measuring step 16).

After that, the calculation unit 52 calculates a temperature rise rate based on the temperature measured by the temperature measurement device 37 (temperature rise rate calculating step 17). The evaluation unit 54 evaluates arc-resistance performance based on the temperature rise rate calculated by the calculation unit 52 and the information stored in the correlated information memory unit 53 (arc-resistance performance evaluating step 18).

Next, arc-resistance performance evaluation carried out based on the method for evaluating arc-resistance performance according to this embodiment will be described with reference to FIG. 9 and FIG. 10.

Test piece 1 is a flame retardant treated synthetic fiber represented by formula $[—C_{10}H_8O_4—]_n$ known as aramid. Test piece 2 is a natural fiber represented by formula $[—C_6H_{10}O_5—]_n$ known as cotton. Both test pieces were irradiated with plasma for five seconds (Time 0 s to 5 s in FIG. 9). Plasma was also irradiated when no test piece was placed for just three seconds (Time 0 s to 3 s in FIG. 9).

Figure 9:
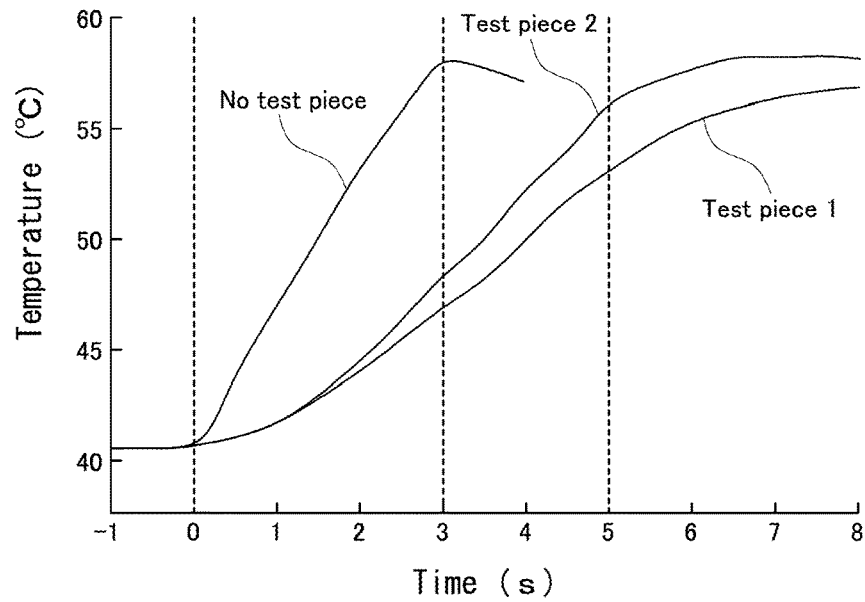
FIG. 9 is a graph of temperature vs time in the method for evaluating arc-resistance performance according to the same embodiment.

FIG. 9 shows a graph of temperature on the back surface of the test piece vs time. The temperature rise rate when no test piece is placed is much higher than the temperature rise rate when the test piece is placed. One can therefore say that heat conduction to the heat conducting part 37b is reduced by the test piece. From this, it can be said that the arc-resistance performance evaluation device 1 according to this embodiment is operating normally enough to be able to investigate the heat resistant effects based on the temperature rise rate.

With a test piece placed, the temperature keeps rising even after the irradiation time (5 seconds) has passed. This is considered to be because it took time until the temperature of the test piece went up by the heat of the plasma. A comparison between the measurement results of Test piece 1 and Test piece 2 shows that the temperature rise rate is about the same until 1.5 seconds have passed, while, after 1.5 seconds have passed, the temperature rise rate of Test piece 1 is lower than that of Test piece 2.

Figure 10:
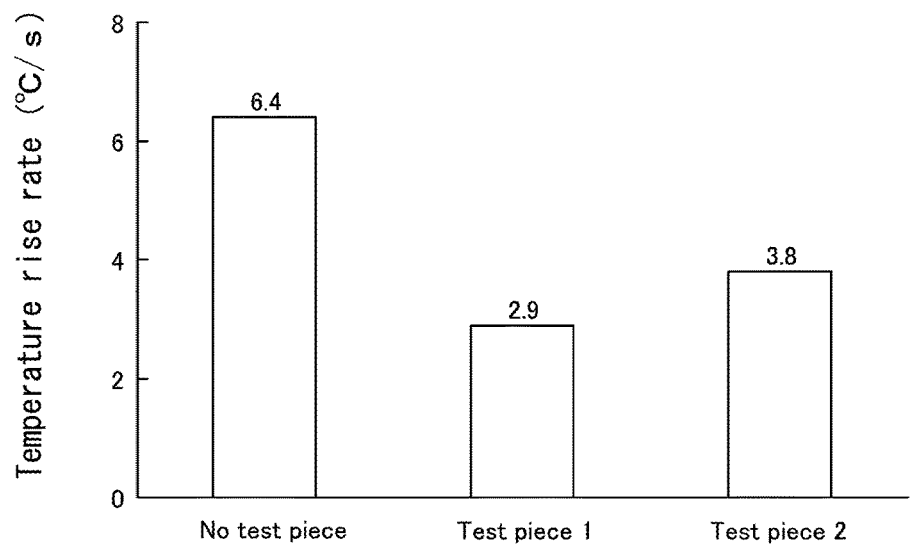
FIG. 10 is a graph comparing temperature rise rates in the method for evaluating arc-resistance performance according to the same embodiment.

FIG. 10 shows the temperature rise rate calculated based on the data shown in FIG. 9. The temperature rise rate is calculated by line shape fitting at a temperature (T1+10%×ΔT) and at a temperature (T1+90%×ΔT), where ΔT is a difference between a temperature T1 before the irradiation of plasma and a maximum temperature T2. The results show that Test piece 1 has a temperature rise rate that is 24% lower than that of Test piece 2. Based on this, Test piece 1 is evaluated to have better arc-resistance performance than Test piece 2.

As described above, according to the method for evaluating arc-resistance performance of this embodiment, the front surface of a sheet-like test piece 10 is irradiated with plasma 100, and the temperature on the back surface of this test piece 10 is measured. A temperature rise rate is calculated based on the measured temperature, and the arc-resistance performance is evaluated based on the calculated temperature rise rate. This way, the arc-resistance performance is evaluated based on the back surface temperature of the test piece 10, so that the arc-resistance performance of protective clothing can be evaluated appropriately based on the heat energy that will be input to the worker wearing the clothing.

According to the arc-resistance performance evaluation device 1 of this embodiment, the plasma generator 21 generates plasma 100, and the stand 31 places the sheet-like test piece in position, whereby the plasma 100 generated in the plasma generator 21 is irradiated on the front surface of the test piece 10. The temperature measurement device 37 then measures the temperature on the back surface of the test piece 10. Arc-resistance performance evaluation based on the back surface temperature of the test piece 10 is thus made possible, so that the arc-resistance performance of protective clothing can be evaluated appropriately based on the heat energy that will be input to the worker wearing the clothing.

According to the arc-resistance performance evaluation device 1 of this embodiment, the plate-like heat conducting part 37b supports the back surface of the test piece 10. The heat conducting part 37b conducts heat of the back surface of the test piece 10 to the thermocouple 37a, and the thermocouple 37a detects the temperature of the heat. This way, the temperature on the back surface of the test piece 10 can be measured accurately.

According to the arc-resistance performance evaluation device 1 of this embodiment, the base body 36 fixes the heat conducting part 37b. The heat insulating part 38 having lower heat conductivity than that of the base body 36 is disposed between the base body 36 and the heat conducting part 37b. This way, the heat conduction from the base body 36 to the heat conducting part 37b is reduced, so that the temperature on the back surface of the test piece 10 can be measured accurately via the heat conducting part 37b with the thermocouple 37a.

According to the arc-resistance performance evaluation device 1 of this embodiment, the calculation unit 52 calculates the temperature rise rate based on the temperature measured by the temperature measurement device 37. The evaluation unit 54 evaluates arc-resistance performance based on the temperature rise rate calculated by the calculation unit 52. This way, the arc-resistance performance is evaluated based on the back surface temperature of the test piece 10, so that the arc-resistance performance of protective clothing can be evaluated appropriately based on the heat energy that will be input to the worker wearing the clothing.

According to the arc-resistance performance evaluation device 1 of this embodiment, inductively coupled thermal plasma is used as the heat source instead of (transferred or non-transferred) arc plasma. As opposed to the arc plasma in which discharge tends to be relatively localized due to the self pinch effect, the inductively coupled thermal plasma according to this embodiment can apply heat flux in a relatively wide area.

Also, the inductively coupled thermal plasma can generate clean plasma since it does not use electrodes to make a discharge and is free of impurities originating from the electrode materials. Furthermore, the inductively coupled thermal plasma is excellent in that the test piece 10 can be irradiated with the plasma at atmospheric pressure, that it is highly controllable, that it allows free adjustment of irradiation power, that it offers good reproducibility, and that it allows direct observation of a contact surface between thermal plasma and the test piece 10.

Moreover, the inductively coupled thermal plasma allows efficient evaluation of the effect of heat generated in an arc incident (heat that passes through the test piece 10) on a human body. In addition, with the inductively coupled thermal plasma, continuous operation is possible since it is a non-electrode discharge, and consequently irradiation can be done for a prolonged time. For these reasons, with the inductively coupled thermal plasma according to this embodiment, arc-resistance performance of a sheet-like test piece 10 can be evaluated stably.

The present invention is not limited to the configuration of the embodiment described above, and the effects are not limited to those described above. It goes without saying that the present invention can be variously modified without departing from the scope of the subject matter of the present invention. Not to mention, the configurations and methods or the like according to various modification examples described below, for example, may be freely selected and adopted to the configurations or methods of the embodiment described above.

The embodiment described above is configured such that the temperature rise rates of a plurality of test pieces 10 are compared and the test piece 10 having a lower temperature rise rate is evaluated to have good arc-resistance performance. The present invention is not limited to such a configuration. For example, the present invention may be configured such that a temperature rise rate is compared to a reference value, and if the temperature rise rate is lower than the reference value, the test piece is evaluated to have good arc-resistance performance. Alternatively, it may be configured such that a test piece is evaluated such that it is given an arc-resistance performance rank based on the temperature rise rate.

The embodiment described above is configured such that the calculation unit 52 calculates the temperature rise rate based on the temperature measured by the temperature measurement device 37, and the evaluation unit 54 evaluates the arc-resistance performance based on the temperature rise rate calculated by the calculation unit 52. The present invention is not limited to such a configuration. For example, the present invention may be configured such that an analyst calculates the temperature rise rate, or that an analyst evaluates the arc-resistance performance based on the temperature rise rate.

The arc-resistance performance evaluation device 1 according to the embodiment described above is configured such that an analyst determines whether or not each of the first to fourth requirements is met, the first requirement being that the flow rate in both gas inlet parts 241 and 242 is in a constant state, the second requirement being that the power supplied to the induction coil 25 is in a constant state, the third requirement being that the pressure inside the tubular part 23 is in a constant state, and the fourth requirement being that the plasma 100 is in a stable state. The arc-resistance performance evaluation device 1 according to the present invention is not limited to such a configuration.

For example, the control unit 4 may be configured such that it makes at least one of the four judgments described above. In particular, the control unit 4 may be configured such that it makes all the four judgments, and causes the stand 31 to be automatically moved by the movable part 32 when all the four requirements have been met.

The arc-resistance performance evaluation device 1 according to the embodiment described above is configured such that the four judgments described above are made when moving the stand 31, but the invention is not limited to such a configuration. For example, it may be configured such that at least one of the four judgments described above is made. The order of judgments is not limited to a particular one.

The arc-resistance performance evaluation device 1 according to the embodiment described above is configured such that the pressure detector 23d detects the pressure inside the tubular part 23. The arc-resistance performance evaluation device 1 according to the present invention is not limited to such a configuration. For example, the arc-resistance performance evaluation device 1 according to the present invention may be configured such that the pressure detector 23d detects the pressure inside the chamber unit 22, or that the pressure detector 23d detects the pressure inside both of the tubular part 23 and the chamber unit 22.

DESCRIPTION OF REFERENCE SIGNS

1: Arc-resistance performance evaluation device
2: Device main body
3: Stand unit
4: Control unit
5: Temperature analysis processing unit
6: Imaging unit
7: Light analysis processing unit
8: Setting value input unit
10: Test piece
21: Plasma generator
22: Chamber unit
23: Tubular part
23a: Inner tube
23b: Outer tube
23c: Passage
23d: Pressure detector
24: Gas inlet
25: Induction coil
26: Power unit
26a: Power detector
26b: Power changer
27: Cold water supply unit
31: Stand
32: Movable part
33: Fixed part
34: Base
35: Cover
35a: Holder
35b: Opening
35c: Groove
36: Base body
36a: Cavity
37: Temperature measurement device
37a: Thermocouple
37b: Heat conducting part
38: Heat insulating part
41: Memory unit
42: Power control unit
43: Incoming flow rate controller
44: Outgoing flow rate controller
51: Measured temperature memory unit
52: Calculation unit
53: Correlated information memory unit
54: Evaluation unit
71: Spectrometer
72: Temperature input unit
73: Basic information memory unit
74: Spectrum calculation unit
75: Spectrum display unit
100: Plasma
221: Chamber
221a: Window
221b: Insertion part
222: Gas outlet
223: Outgoing flow rate changer
241: First gas inlet part
241a: Incoming flow rate detector
241b: Incoming flow rate changer
242: Second gas inlet part
242a: Incoming flow rate detector
242b: Incoming flow rate changer

The invention claimed is:

1. A method for evaluating arc-resistance performance comprising:
    irradiating a front surface of a sheet-like test piece with plasma;
    measuring a temperature on a back surface of said test piece irradiated with the plasma;
    calculating a temperature rise rate based on the measured temperature; and
    evaluating arc-resistance performance based on the calculated temperature rise rate.

2. The method for evaluating arc-resistance performance according to claim 1, wherein
    said plasma is inductively coupled thermal plasma.

3. An arc-resistance performance evaluation device comprising:
    a plasma generator that generates plasma; and
    a stand on which a sheet-like test piece is placed so that the plasma generated in the plasma generator is irradiated on a front surface of said test piece,
    wherein said stand includes a temperature measurement device that measures a temperature on a back surface of said test piece, said temperature measurement device including a thermocouple that detects temperature, and a flat plate-like heat conducting part that supports the back surface of said test piece and conducts heat from the back surface of said test piece to said thermocouple, and
    wherein said stand includes a base body for fixing said heat conducting part, and a heat insulating part having lower heat conductivity than that of said base body and disposed between said base body and said heat conducting part.

4. The arc-resistance performance evaluation device according to claim 3, further comprising
    a calculation unit that calculates a temperature rise rate based on the temperature measured by said temperature measurement device; and
    an evaluation unit that evaluates arc-resistance performance based on the temperature rise rate calculated by said calculation unit.

5. The arc-resistance performance evaluation device according to claim 3,
    wherein said plasma is inductively coupled thermal plasma.

6. An arc-resistance performance evaluation device comprising:
- a plasma generator that generates plasma;
- a stand on which a sheet-like test piece is placed so that the plasma generated in the plasma generator is irradiated on a front surface of said test piece, wherein said stand includes a temperature measurement device that measures a temperature on a back surface of said test piece;
- a calculation unit that calculates a temperature rise rate based on the temperature measured by said temperature measurement device; and
- an evaluation unit that evaluates arc-resistance performance based on the temperature rise rate calculated by said calculation unit.

7. The arc-resistance performance evaluation device according to claim 6, wherein
- said temperature measurement device includes a thermocouple that detects temperature, and a flat plate-like heat conducting part that supports the back surface of said test piece and conducts heat from the back surface of said test piece to said thermocouple.

8. The arc-resistance performance evaluation device according to claim 6,
- wherein said plasma is inductively coupled thermal plasma.

* * * * *